US006925847B2

(12) United States Patent
Motsenbocker

(10) Patent No.: US 6,925,847 B2
(45) Date of Patent: Aug. 9, 2005

(54) HAND HELD STENT CRIMPING APPARATUS AND METHOD

(76) Inventor: Thomas Motsenbocker, 3305 S. Skye Way, Flagstaff, AZ (US) 86002

( * ) Notice: Subject to any disclaimer, the term of this patent is extended or adjusted under 35 U.S.C. 154(b) by 0 days.

(21) Appl. No.: 10/654,536

(22) Filed: Sep. 2, 2003

(65) Prior Publication Data

US 2004/0128818 A1 Jul. 8, 2004

Related U.S. Application Data

(60) Provisional application No. 60/407,403, filed on Aug. 31, 2002.

(51) Int. Cl.[7] .............................................. B21D 39/04
(52) U.S. Cl. ...................... 72/402; 72/409.19; 29/283.5
(58) Field of Search ............................. 72/402, 409.19; 29/237, 282, 283.5

(56) References Cited

U.S. PATENT DOCUMENTS

| | | | | |
|---|---|---|---|---|
| 2,079,498 A | * | 5/1937 | Douglas ...................... | 72/402 |
| 3,203,078 A | * | 8/1965 | Ustin .......................... | 29/862 |
| 3,252,316 A | * | 5/1966 | Haucke ....................... | 72/402 |
| 3,335,598 A | * | 8/1967 | Jessen ......................... | 72/402 |
| 3,459,029 A | * | 8/1969 | Rosenfeld et al. ............ | 72/402 |
| 3,713,322 A | * | 1/1973 | Fischer ...................... | 72/409.09 |
| 4,644,777 A | * | 2/1987 | Kumeth ....................... | 72/402 |
| 4,727,742 A | * | 3/1988 | Weaver ........................ | 72/402 |
| 5,261,263 A | * | 11/1993 | Whitesell ................... | 72/409.19 |
| 6,176,116 B1 | * | 1/2001 | Wilhelm et al. ........... | 72/409.12 |
| 6,629,350 B2 | * | 10/2003 | Motsenbocker ............ | 29/283.5 |

* cited by examiner

*Primary Examiner*—Daniel C. Crane
(74) *Attorney, Agent, or Firm*—Skinner and Associates

(57) ABSTRACT

A hand actuatable apparatus and method for crimping a stent or processing other articles by segmental radial compression. The apparatus includes a stationary base housing; a rotatable drive hub which is moveable in relation to the base housing; a crimping head communicatively coupled to the base housing and to the drive hub; and an actuator handle connected to the base housing and to the drive hub. The crimping head includes a plurality of segments oriented about a center aperture which receives a stent or article to be compressed. The segments each have a proximal end and an angled distal end with at least one angled side face terminating in an edge of a predetermined length and defining the center aperture. Actuation of the handle rotates the drive hub, which causes the segments to move and pivot, resulting in closure of the center aperture and compression of the stent or other article.

15 Claims, 10 Drawing Sheets

◁— CLOSE DIRECTION

HAND HELD STENT CRIMPING APPARATUS AND METHOD

CROSS-REFERENCE TO RELATED APPLICATIONS, IF ANY

This application claims the benefit under 35 U.S.C. §119 (e) of U.S. Provisional Patent Application Ser. No. 60/407,403, filed Aug. 31, 2002, which is hereby incorporated by reference.

37 C.F.R. §1.71(E) AUTHORIZATION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention

The present invention relates, generally, to medical devices and medical device manufacturing apparatus and methods. Additionally, the invention relates to holding, compressing, and crimping devices. More particularly, the invention relates to medical stent crimping devices. The invention has particular utility in the medical industry as a device and method for uniformly crimping a balloon expandable or self-expanding metal or non-metallic stents or stent grafts by a hand held apparatus or hand implementable method.

2. Background Information

The state of the art includes various stent crimping devices and methods. The devices include a collet style crimp mechanism, a flat rolling plate style crimp mechanism, loop or coil radial compression (U.S. Pat. No. 6,063,102), a funnel tube style crimping mechanism (U.S. Pat. No. 5,992,000 FIG. 3), a Touhy style silicone elastomeric crimp sleeve (U.S. Pat. No. 6,009,614), and an expandable bladder/elastic tube. The flat rolling plate style crimp mechanism includes an elastomeric surface upon which the stent in place, and a flat plate positioned and adapted to roll over the stent. Weight may be added onto the plate. The rolling action crimps the stent in place somewhat akin to rolling out dough. The expandable bladder is shaped as a sleeve. Fluid is pumped into the bladder to rotatably compress the stent positioned in it. Other U.S. patents directed to stent crimping technology include U.S. Pat. Nos. 6,063,092, 6,051,002, 6,024,737, 6,018,857, 5,951,540, 5,931,851, 5,672,169, 5,672,169 and 5,626,604. These patents provide background information on stent technology in general and are incorporated by reference for that reason.

The known stent crimper devices and methods are believed to have significant limitations and shortcomings. For example, their structure (i.e. bore size in the structure) limits the diameter of the stent. Additionally, they are not able to use a simple process to satisfy the tolerance demands for certain medical applications. For example, they may not be able to accurately, consistently and uniformly crimp the stent in a single step. This is particularly true of stents with small diameters. For this and other reasons, a need exists for the present invention.

U.S. patent application Ser. No. 09/877,469, filed Jun. 8, 2001, entitled STENT CRIMPING APPARATUS AND METHOD, filed Jun. 8, 2001 discloses table top, powered and automatic stent crimping apparatus and methods.

This invention provides a hand held stent crimper device and method which are believed to fulfil the need and to constitute an improvement over the background technology. The device and method of the present invention makes it possible through a simple process to crimp a balloon expandable or self-expanding metal or non-metallic intravascular or other anatomically placed stents. The present invention does not require a fixed bore size (I.D.) to obtain the final crimped stent profile. The present invention can be designed to crimp operably receive stents having diameters from 12 mm (0.47 in.) to near zero. It has been found that, to optimize the present invention to crimp coronary stents, the device should be designed to handle stents between 5 mm to 0.5 mm. The present invention is capable of holding tolerances to 0.005" while providing a uniform extended crimp of between 2 mm (0.08 in.) and 100 mm (3.94 in.) in length.

Benefits of this technology, in general, include a reduced cycle time, reduced machine size, repeatability of the crimped stent diameter, security of the crimped stent, and the elimination of a fixed bore size (I.D.) during the crimp process.

The stent crimping apparatus and method of this invention are particularly useful for engineers, clinical research workers, and pre-clinical catheterization laboratory workers.

All US patents and patent applications, and all other published documents mentioned anywhere in this application are incorporated by reference in their entirety.

BRIEF SUMMARY OF THE INVENTION

The present invention provides a hand held crimping device and method which are well suited for crimping medical stents.

In one embodiment, the invention provides a hand held radial compression apparatus for compressing an article, for example crimping a stent. The apparatus includes a stationary base housing; a rotatable drive hub which is moveable in relation to the base housing; a crimping head communicatively coupled to the base housing and to the drive hub; and an actuator handle connected to the base housing and to the drive hub. The crimping head includes a plurality of segments oriented about a center aperture which receives a stent or article to be compressed. The segments each have a proximal end and an angled distal end with at least one angled side face terminating in an edge of a predetermined length and defining the center aperture. Actuation of the handle rotates the drive hub, which causes the segments to move and pivot, resulting in closure of the center aperture and compression of the stent or other article.

In another aspect the invention provides an apparatus for engaging an article, comprising:
  a housing;
  at least one rotatable member communicatively coupled and moveable in relation to the housing;
  a radial compression mechanism communicatively coupled and moveable in relation to the housing, and a hand operable actuator communicatively coupled to the housing and the rotatable member.

In yet another aspect, the invention provides a hand actuatable apparatus for radially engaging and compressing an article such as crimping a stent, comprising (a) a housing including a cylindrical body with at least one axially disposed central aperture adapted to receive the article to be engaged;

(b) at least one rotatable member communicatively coupled and moveable in relation to the housing, the rotatable member having a ring configuration which at least partially surrounds the radial compression member, the rotatable member further having an arm member;

(c) a radial compression mechanism communicatively coupled and moveable in relation to the housing, the radial compression member comprising a plurality of segments, each having a predetermined shape with a proximal end and a distal end, each segment having a centerline between the proximal and distal ends, each segment having a proximal point and a distal point, one said point being disposed on the centerline and one said point being disposed off the centerline, and one said point being pivotally coupled to the housing and one said point being pivotally coupled to the rotatable member, the segments being arranged so that the segment distal ends are disposed adjacent to and a predetermined distance away from a central point, and that the segment centerlines extending therefrom toward the segment distal ends are oriented away from the central point, and the segment distal ends moving closer to the central point upon rotation of the rotatable member in a predetermined direction; and (d) a hand operable actuator communicatively coupled to the housing and the rotatable member, the actuator comprising a cam linkage connected to the arm member of the rotatable member, a first arm connected to the cam linkage, and a second arm connected to the cam linkage and movable in relation to the first arm member.

The features, benefits and objects of this invention will become clear to those skilled in the art by reference to the following description, claims, and drawings.

DETAILED DESCRIPTION

Figure 1:
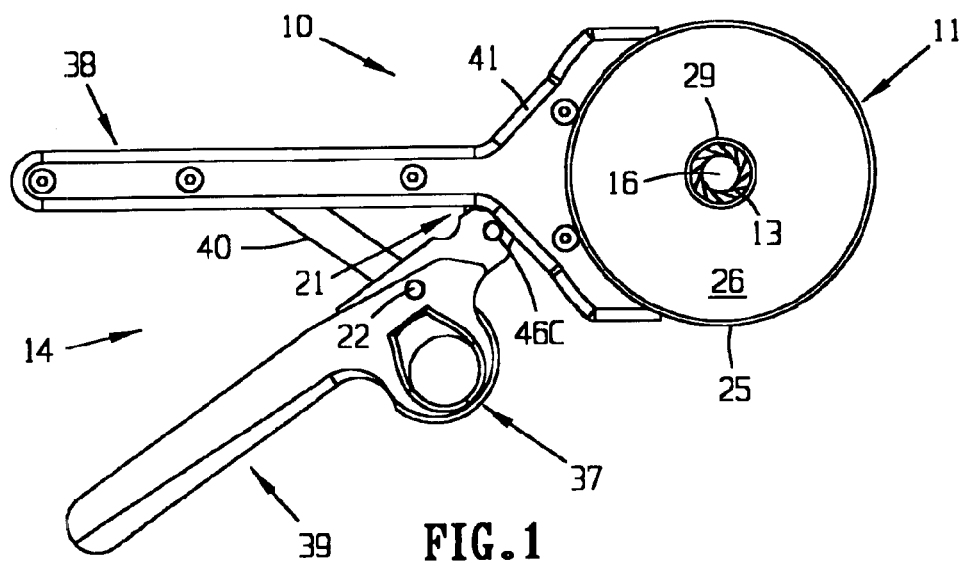
FIG. 1 is a front, plan view of an embodiment of the hand actuatable stent crimping apparatus of the present invention.
Figure 2:
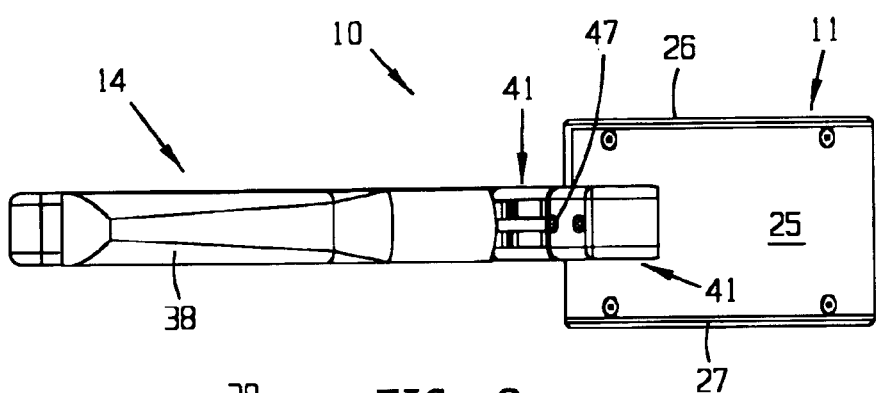
FIG. 2 is an elevation view thereof.
Figure 3:
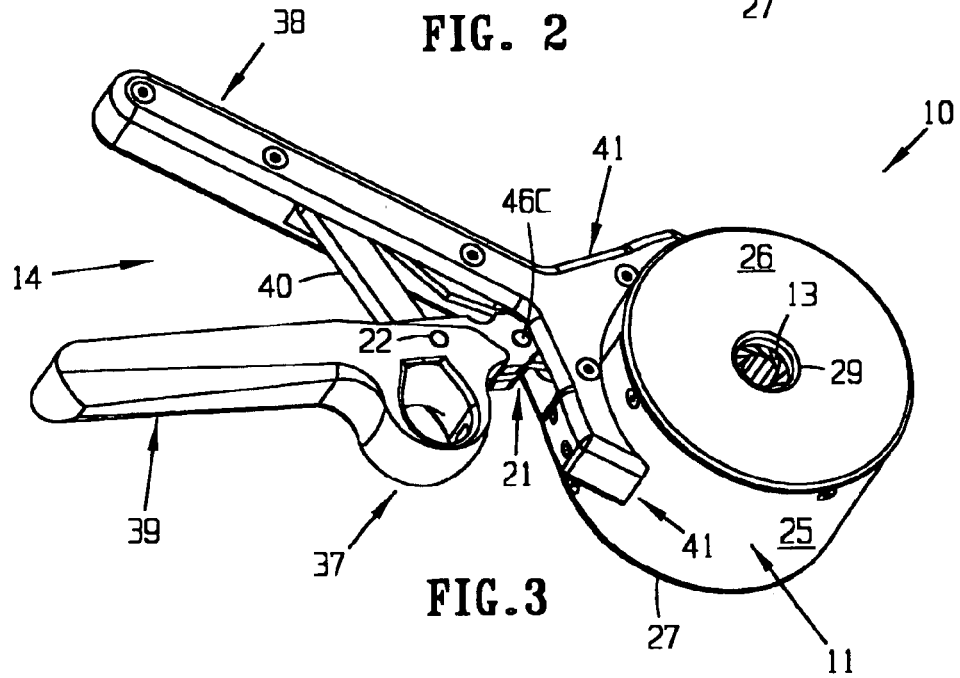
FIG. 3 is perspective view thereof.

The hand held stent crimping device and method is suitable to uniformly crimp a balloon expandable or self-expanding metal or non-metallic stents or sent grafts. A crimped stent includes a core such as a balloon catheter and a sheath. The stent is uniformly crimped to the collapsed balloon along the length, preferably within a diameter tolerance of 0.005 inches. The apparatus and methods of the invention may also be used or adapted for use in securely gripping, holding and/or selectively radially compressing other articles. The apparatus and methods are also useable or adaptable for use in crease and/or fold structures such as balloons, to form a wide variety of radial compression devices (such as within a machining center so that the machinists will not have to replace collets), and to form or create a stent retention mechanism that retains the stent without applying radial forces against the balloon, thus enabling the balloon or sheath to be retracted.

Referring to FIGS. 1–5, an embodiment of the apparatus 10 for crimping stents or radially compressing other articles generally includes a stationary base 11, a rotatable activation hub 12, a plurality of segments forming a multi-part radial compression mechanism or wedge 13, and an actuation handle 14. The base 11 houses the plurality of segments 15, (preferably twelve (a–l), but at least three) and is communicatively connected to them via pivot pins 19a–l. The rotatable activation hub 12 is also communicatively connected to the segments 15a–l via drive pins 20a–l. The segments 15a–l are communicatively linked to the base 11 and the activation hub 12 via the pivot 19 and drive 20 pins, respectively. The actuation handle 14 is communicatively connected to the activation hub 12 via a linkage 21. The actuation handle 14 is hand operated by an operator. Compression wedge 13 has a central aperture 16 with a variable diameter (shown substantially open in FIG. 1 and substantially closed in FIG. 5). In use, a stent or other article is placed in the aperture 16, and the crimper 10 is actuated to close the aperture 16 and radially compress the stent.

Additional sub-systems, assemblies or mechanisms (not shown) may be added to the basic apparatus outlined above. These additional systems include, but are not limited to handling and alignment control and/or indication devices, pressure regulation and/or indication systems, calibration systems, control devices such as mechanical stops, vision assistance, laser micrometers, interchangeable crimp heads, and the like.

The base or housing 11 has a cylindrical configuration with a predetermined diameter and length (or thickness). The base preferably consists of a cylindrical body 25, a circular top cap 26, and a circular bottom cap 27 which define an interior space or chamber 28 of a predetermined volume. One of the caps may be fixed to the body. The caps or covers 26 and 27 have centrally disposed apertures 29 and 30. The housing 11 provides a stationary base for mounting of the segments 15 and relative to which the segments 15 move, and further shelters and contains the wedge 13. The base body 25 preferably has a passage 24 for mating of the handle elements 14, and which is partially covered by shroud 23 of top 26. The base 11 may be constructed of a rigid material or materials such as a metal, for example stainless steel, or a polymeric material, for example polycarbonate or PEEK.

Figure 4:
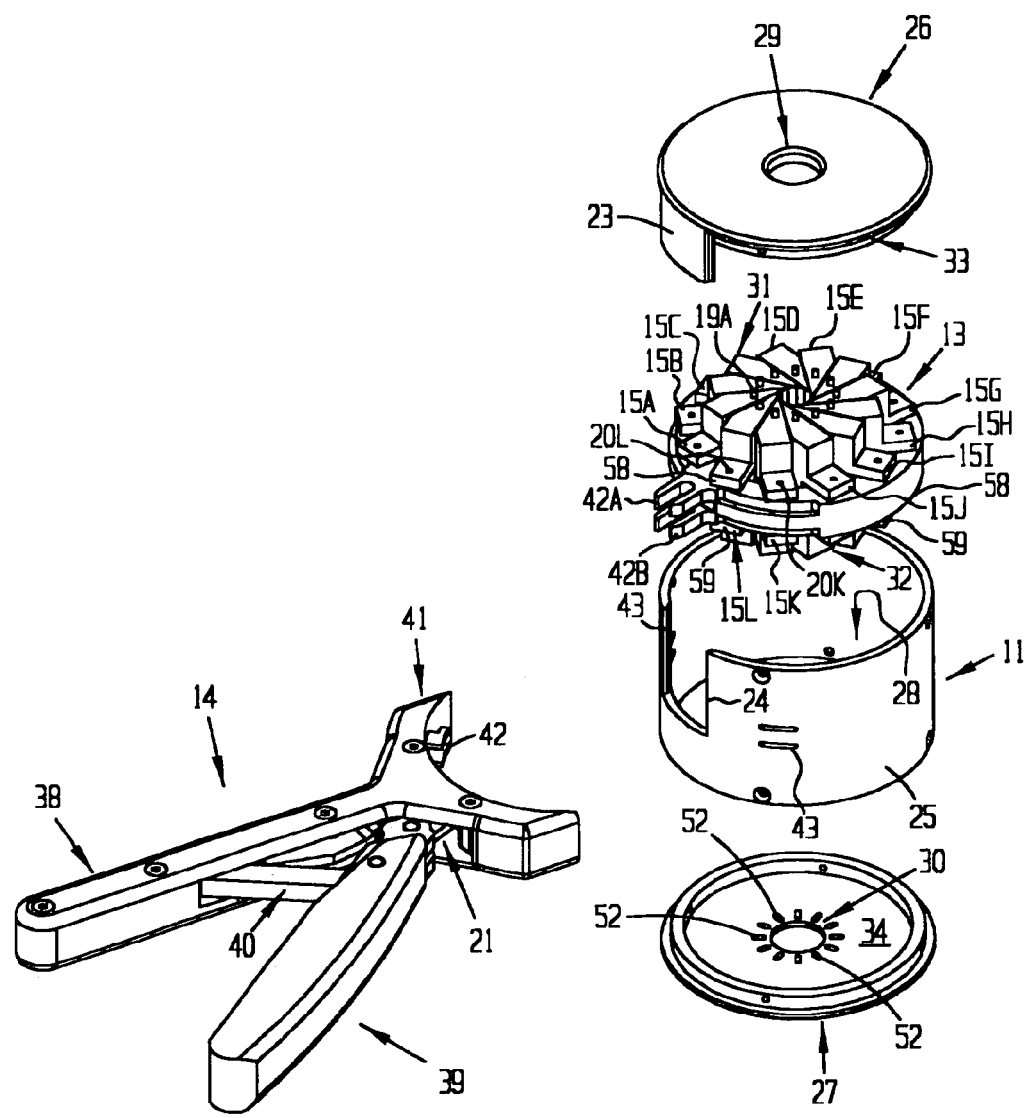
FIG. 4 is an exploded view thereof.

The activation hub 12 constructed of rigid material, such as those discussed with respect to the housing. The hub 12 is disposed in the housing interior 28 and has a ring type configuration with a predetermined thickness and a predetermined outside diameter slightly less than the inside diameter of the housing 11. The hub 12 is rotatable with respect to the base 11. When the hub 12 is operatively disposed in the housing chamber 28, its front and rear faces 31 and 32 are approximately flush with the inside walls of the caps 26 and 27. The hub 12 preferably has a pair of slotted arms 42a/b for actuatable coupling with the linkage 21. As is shown in FIG. 4, the slots have an optional open end for detachment of a disposable head.

Figure 5:
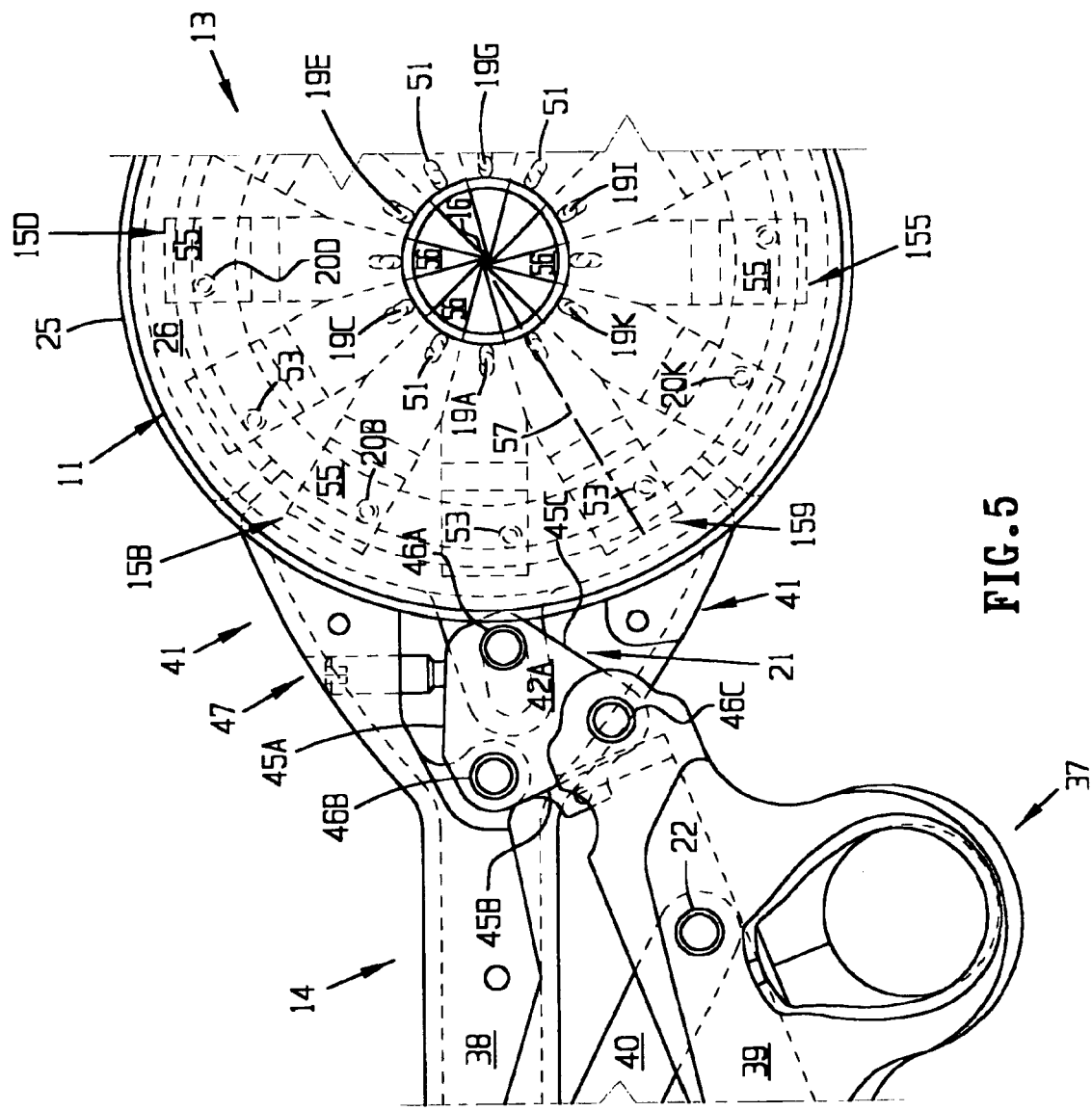
FIG. 5 is a detailed view of a portion of the apparatus of FIG. 1.

The actuation handle 14 preferably comprises a first arm member 38 fixed to and extending from the housing 11, the linkage 21 coupled to the hub 12 and to the first arm member 38, a second arm member 39 pivotally connected to the linkage 21, and a connecting arm 40 pivotally connected to the first and second arm members 38 and 39. The first arm member 38 has a predetermined elongated configuration and length and is preferably connected to the housing 11 by a bracket portion 41 which is integrally formed with the housing 11. Alternatively, as is best shown in FIG. 4, the bracket portion 41 may be detachable from the housing 11 via connection tabs 42 and slots 43 or the like to provide a disposable housing/wedge/hub head assembly. The second arm member 39 has a predetermined elongated configuration and length and is pivotally connected to the linkage 21 at post 46c. Second arm member 39 may have an optional finger guide 37. Connecting arm 40 has a predetermined elongated configuration and length and is pivotally connected to first and second arm members 38 and 39. As is best shown in FIG. 5, the linkage 21 preferably has a triangular configuration with three sides 45a–c and three pivot posts 46a–c. The linkage 21 functions as a cam to move the hub 12. Pivot post 46a is pivotally and slidably disposed in slotted arms 42, post 46b is pivotally coupled to first arm 38, and post 46c is pivotally coupled to second arm 39. Stop member 47 is disposed in bracket portion 41 to provide an adjustable stop to limit pivotal movement of the linkage (via contact with side 45a) 21 and hence, the degree of rotation of the hub 12 and aperture 16 closure.

The segments 15a–l cooperatively form the wedge 13, which has a roughly cylindrical configuration with a predetermined maximum length or thickness and a circumference such that it is housed within the housing 11. The cooperating width (or thickness) and circumference of the housing 11 interior 28, permit the wedge 13 to move within the interior 28 during a crimping or other radial compressing operation.

The pivot pins 19a–l are constructed of a rigid material, preferably metallic. The pivot pins 19 are cylindrical and have a predetermined length and diameter. The pivot pins are preferably disposed through the segments and extend a predetermined distance out each end side thereof to seat in elongated slots 51 and 52 in the respective interior walls 33 and 34 of the respective caps 26 and 27. The extended ends of the pins 19 mate with slots 51 and 52 and are held therein via a frictional fit. The slots 51 and 52 have predetermined circumference and length and are disposed in a circular pattern equally spaced apart a predetermined distance from each other and from the center of the wedge chamber 28, and radially aligned therewith. Alternatively, a set of top and bottom pivot pins may be used in place of a single pin.

The drive pins 20a–l are constructed of a rigid material, preferably metallic, and have a cylindrical configuration with a predetermined length and diameter. The drive pins 20 are disposed through the segments 15 and extend through bores 53 in the hub 12. Each bore 53 preferably has a cylindrical configuration to pivotally capture a pin 20. The 53 are disposed in a circular pattern equally spaced apart a predetermined distance from each other and from the center axis of the hub 12.

Each segment preferably has a rectilinear configuration with a proximal end 55, a distal end 56. A proximal end 55 preferably has a pair of flat and rectangular tail segments 58 and 59. The tail segments 58 and 59 are separated a predetermined distance. The hub 12 is disposed between the tail segments 58 and 59. The distal end 56 of each segment 15 preferably terminates in a thin edge formed at the intersection of side faces, at least one of which is angled. Although the distal end 56 has a rectilinear, flat and uniform dimensions with a particular dimension, it may be alternatively configured with a curvilinear, non-flat, textured, and/or non-uniform surfaces (such as stepped geometries and various specialized surface textures, for example) in a variety of dimensions, including a truncated end, to provide particular gripping, compression or crimping function and depending upon the article configuration and material. The width of edge is variable between approximately 2 and 100 mm and is based upon the length of the stent to be crimped or article to be engaged, held and/or radially compressed. Preferably, both side faces are angled and equivalent. Optionally the face may have an incut portion to provide tip angle tolerance during disactuation of the wedge 13. The segments 15 have a proximal lower portion and a distally oriented raised or extended portion. A combination of the raised portions of the faces of all of the segments yields center face portion 31. Center portion 31 provides optimum wedge 13 stability with minimal friction within the housing 11. As is discussed in detail below, pin offset location from centerline 75 provides tolerance for movement of the segments 15 through the operating range of the crimping wedge 13. This tolerance permits opening and closing of the crimping head 13.

The segments 15 may be constructed of a polymeric material such as Delrin or Delrin AF, polycarbonate, PEEK or Ertalyte. Alternatively, they may be constructed of a thermoplastic material, a ceramic material, a composite material, or a metallic material such as stainless steel.

In operation, the wedge 13 has an initial, fully open state with the centrally disposed crimping aperture 16, a fully closed state, wherein the aperture 16 has a minimum size, and a plurality of intermediate states between the initial fully open state and the fully closed state wherein the aperture 16 becomes progressively smaller. The maximum diameter of the aperture 16 is variable. The minimum diameter is also variable, approaching zero, and can be set via adjustment screw 47. The length or depth of the aperture 16 is also variable. A stent to be crimped or another article to be engaged and/or radially compressed is inserted and longitudinally advanced a desired distance into the aperture 16 in the initial, open state. The stent is crimped by moving the second arm member 39 towards the first arm member 38. Connecting arm 40 pivotally urges pivot post 46c forward towards the housing 11 causing the linkage body 21 to simultaneously pivot about post 46b. Pivot post 46a simultaneously pivots and moves in slot 42. This combination of arm 14 and linkage 21 movement rotates the hub 12 clockwise, which contracts the aperture 16. Contraction causes the aperture wall to contact and exert a radially compressive force on the stent. The stent diameter is reduced a desired amount and engages a catheter body or another structure as desired in a stent manufacturing process. At the desired reduced diameter, the actuator 14 second arm member 39 is held in position for a desired dwell time. Subsequently, the second arm member 39 is released and a spring or other biasing means connected from post 22 to first arm 38 preferably causes it to move away. This causes the linkage 21 to move in the opposite manner to that described above and causes the hub 12 to move counterclockwise and expand the aperture 16, which releases engagement of the stent. The stent and related structure is retracted and removed from the aperture 16.

The crimping aperture 16 has a substantially circular horizontal dimension and a predetermined length which yields a substantially cylindrical longitudinal dimension. As the aperture 16 contracts and becomes smaller, the periphery of the aperture 16 radially moves towards the longitudinal center axis of the aperture 16 in a substantially uniform manner, whereby the aperture 16 wall maintains a substantially cylindrical configuration through the closing process. Uniform compression is the result of the interaction primarily of the plurality of segments 15 and the pins 19 and 20, in concert with the respective base 11 and hub 12. In an open state, where aperture 16 exists, the centerlines 57 of the respective segments 15 do not radially extend out from the central axis point of the aperture 16. During actuation, the centerlines 57 converge towards the central axis. In the fully closed state, the centerlines 57 extend radially outward from the central axis point. This process brings the distal portions 56 of the segments 15 closer to the center until ultimately the distal most portion of each segment 15, in this embodiment the edges, essentially contact the central axis point. Due to the symmetry of the wedge 13 elements, each segment 15 behaves substantially identically, and the closure process is highly uniform.

The above mentioned segmental centerline 57 convergence process result from pivotal movement of the distal portion 56 of each segment 15 with respect to the proximal portion 55 of the segments 15. The drive hub 12 rotates clockwise with respect to the stationary base 11. The proximal portions 55 of the segments 15 are moved or driven by the drive hub 12, which is pivotally coupled to each segment 15 by the off-centerline drive pins 20 mated with segmental drive pin slots 53. The distal portions 56 of the segments 15 are held in a substantially stationary position, but allowed to pivot, by the base 11 which is coupled to each segment 15 by on-centerline pivot pins 19 mated with slots 51 and 52. The pivot pins 19 are permitted a slight amount of radial movement via radially elongated slots 51 and 52.

Referring to FIGS. 9–16, an alternative embodiment of the segmental radial compression apparatus 110 and process of the present invention has a wedge 113 which has proximally driven, on-centerline drive pins 120 and distal, off-centerline pivot pins 119. Wedge 113 has segments 115. Proximal portions 155 of the segments 115 are coupled in this embodiment to a pair driven (clockwise rotatable) ring shaped hub plates 112a and b by drive pins 120 which are disposed on the centerline of each segment 115. Drive pins 120 extend through bores 153 in the segments 115. Distal portions 156 of the segments 115 are pivotally coupled to a stationary base (not shown) by pivot pins 119 which are disposed off the centerline 157. Pivot pins 119 are disposed through pivot pin bores 151 in the segments 115. Also in this embodiment of the wedge 113, the segments have a single proximal tail portion 158, which is disposed between two hub plates 112a and b. This wedge 113 may be substituted with minor modifications with the housing and handle actuator shown and described with respect to FIGS. 1–5.

Figure 6:
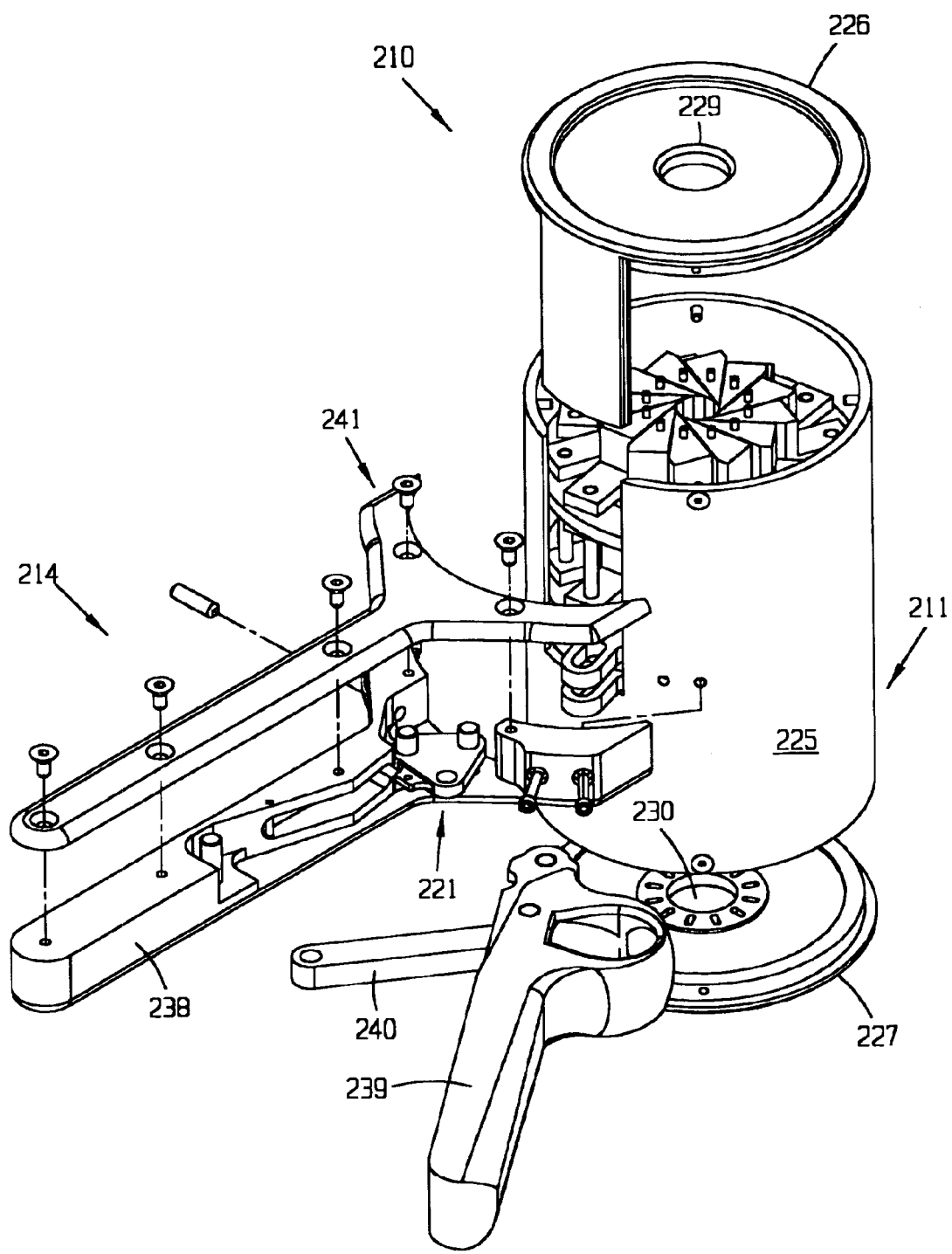
FIG. 6 is a partially exploded view of an alternative embodiment of the apparatus of the present invention.
Figure 7:
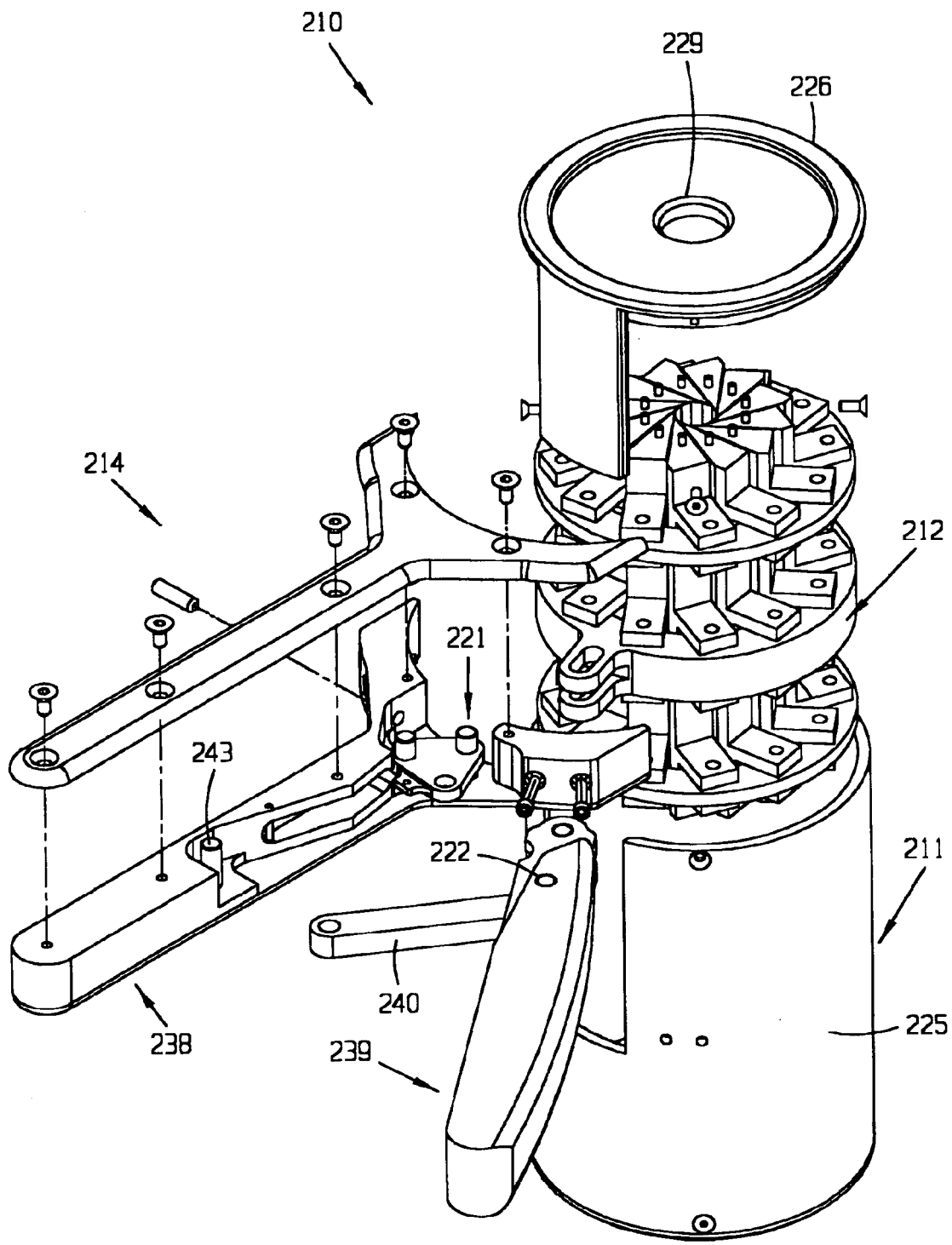
FIG. 7 is further exploded view thereof.
Figure 8:
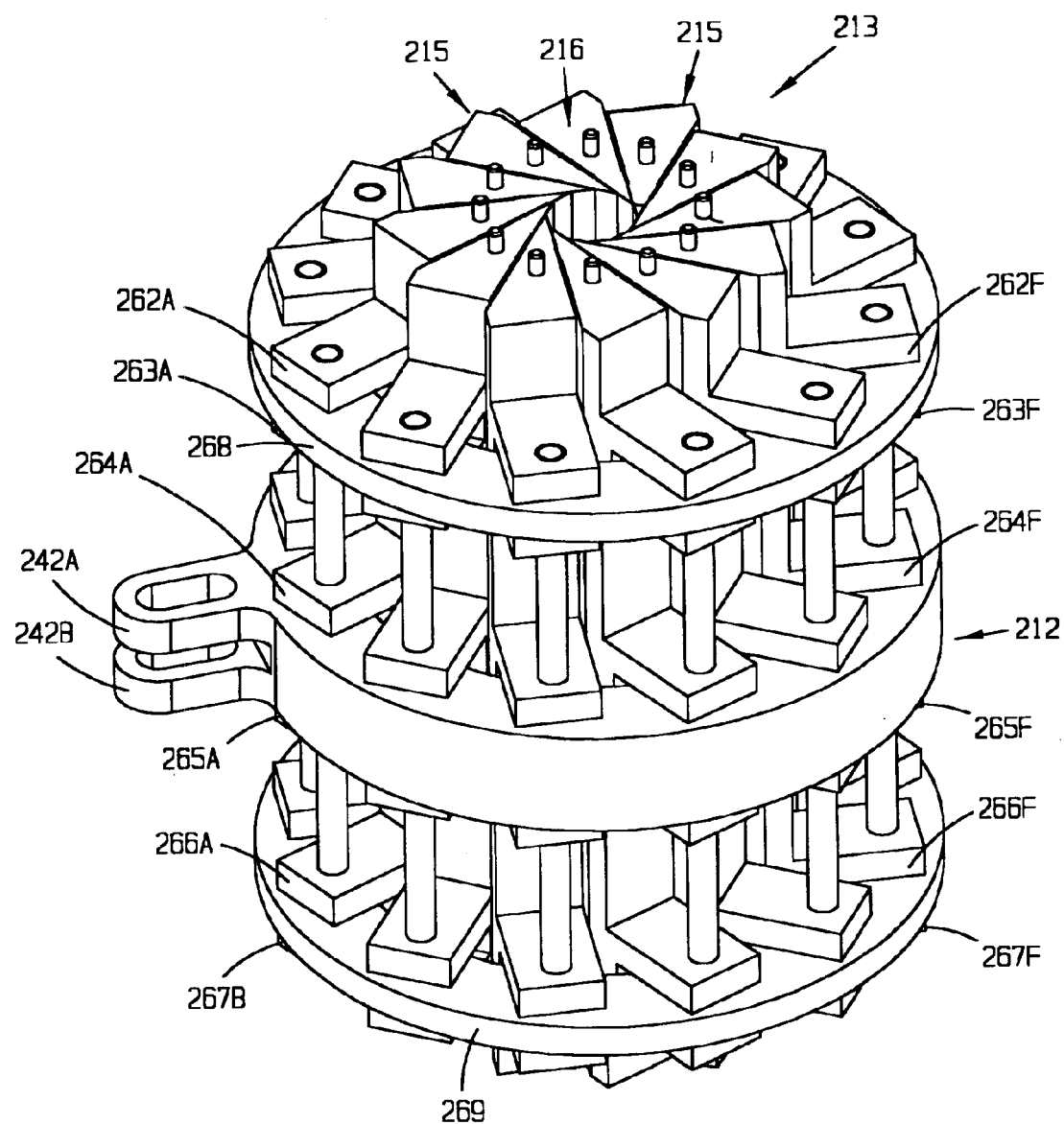
FIG. 8 is a perspective view of a portion thereof.
Figure 10:
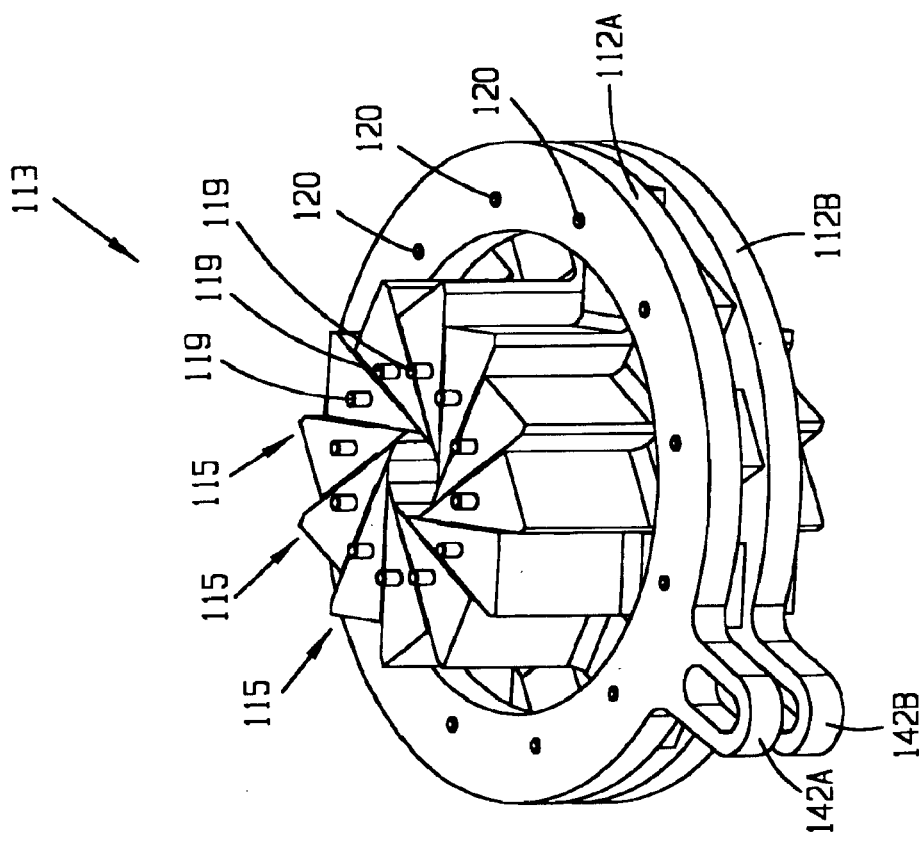
FIG. 10 is a perspective view thereof.
Figure 9:
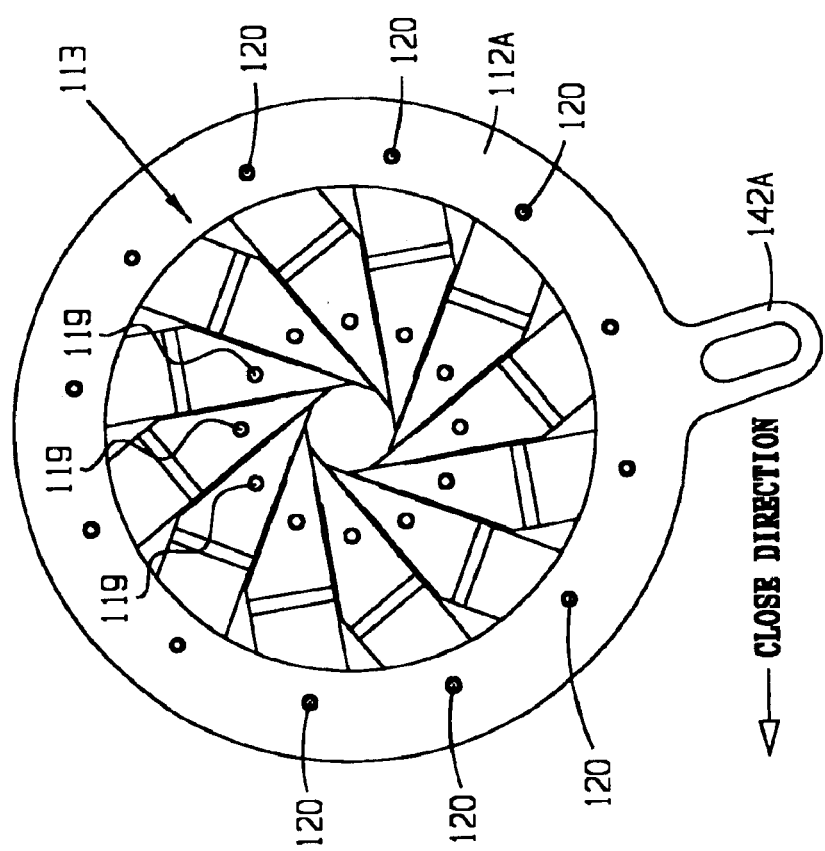
FIG. 9 is a plan view of a portion of yet another alternative embodiment of the apparatus of the present invention.
Figure 11:
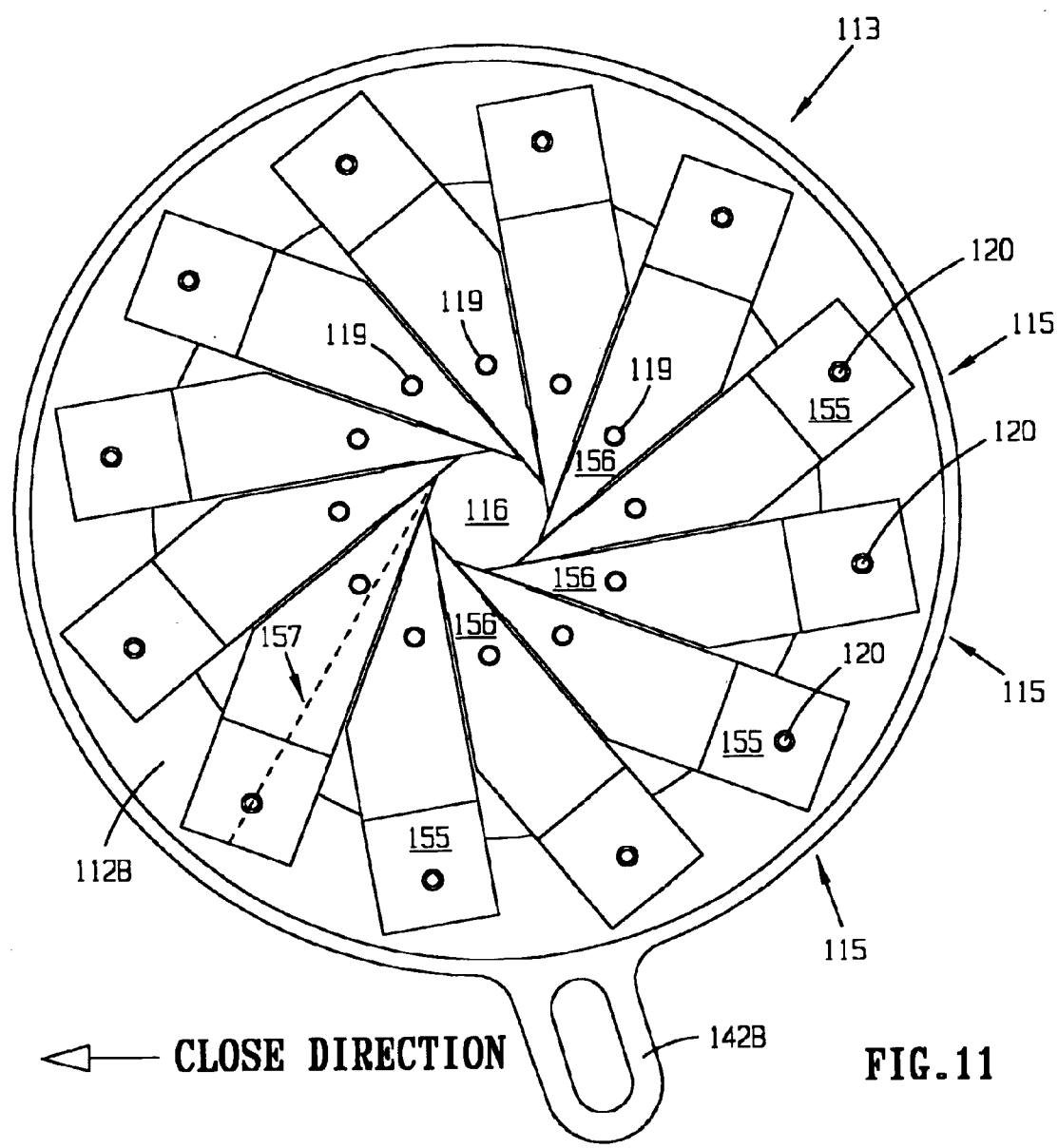
FIG. 11 is a detailed plan view thereof.
Figure 12:
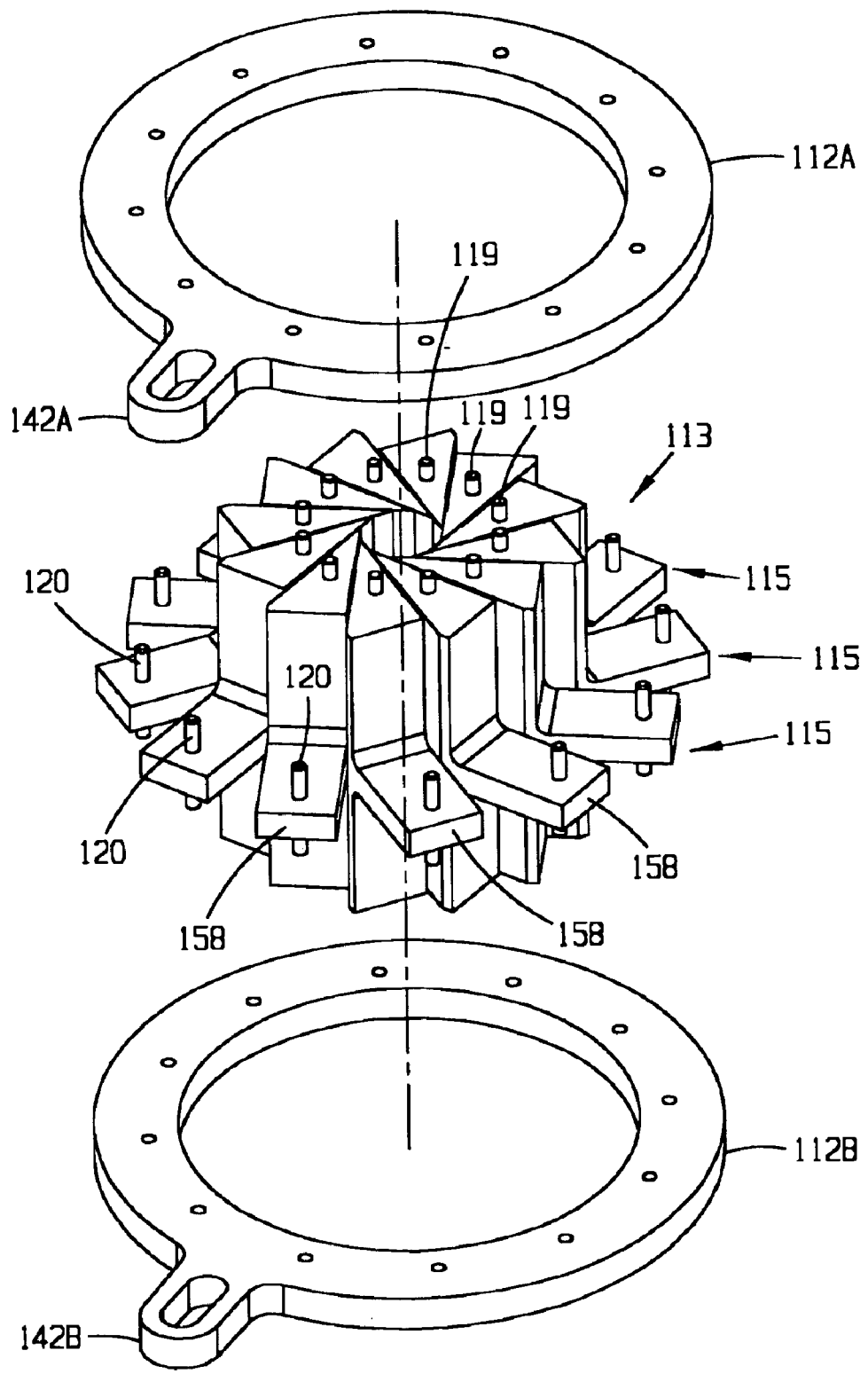
FIG. 12 is an exploded view thereof.
Figure 13:
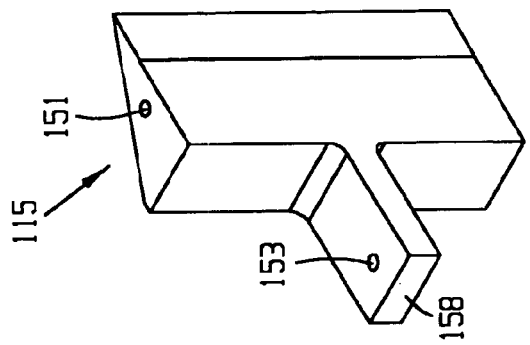
FIG. 13 is a perspective view of an embodiment of a segment of the apparatus of the present invention.
Figure 14:
FIG. 14 is a front elevation view thereof.
Figure 15:
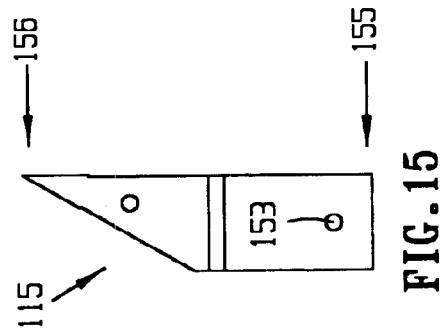
FIG. 15 is a plan view thereof.
Figure 16:
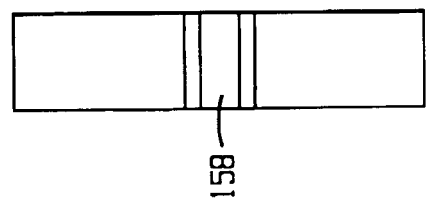
FIG. 16 is an end elevation view thereof.

Referring to FIGS. 6–8, an alternative embodiment of the segmental radial compression apparatus 210 and process of the present invention has a wedge 213 which has an extended width for processing of long stents or articles, for example those up to 100 mm in length.

The apparatus 210 for crimping stents or radially compressing other articles generally includes a stationary base 211, a rotatable activation hub 212, a plurality of 215 segments forming the multi-part radial compression wedge 213, and an actuation handle 214. The base 211 houses the plurality of segments 15, (preferably twelve (a–l), but at least three) and is communicatively connected to them via pivot pins 219a–l. The rotatable activation hub 212 is also communicatively connected to the segments 215a–l via drive pins 220a–l. The segments 215a–l are communicatively linked to the base 211 and the activation hub 212 via the pivot 219 and drive 220 pins, respectively. The actuation handle 14 is communicatively connected to the activation hub 212 via a linkage 221. The actuation handle 214 is hand operated by an operator. Connecting arm 240 is connected to second arm 239 at post 222 and to first arm 238 at connection post 243. Compression wedge 213 has a central aperture 216 with a variable diameter. Except as where indicated, this embodiment of the apparatus 210 has substantially all of the elements of the apparatus 10 shown and described with respect to FIGS. 1–5, and such elements are substantially similar with the exception of size in some cases.

As is best shown in FIG. 8, each segment 215 has a pair of upper proximal tails 262 and 263, a pair of central proximal tails 264 and 265, and a pair of lower proximal tails 266 and 267. Distal drive pins 219 are aligned and disposed through each tail 262–267. In addition to passing through drive hub 212, the pins 219 pass through alignment rings 268 and 269.

The descriptions above and the accompanying drawings should be interpreted in the illustrative and not the limited sense. While the invention has been disclosed in connection with an embodiment or embodiments thereof, it should be understood by those skilled in the art that there may be other embodiments which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

The invention claimed is:

1. An apparatus for engaging an article, comprising:
a housing;
at least one rotatable member communicatively coupled and moveable in relation to the housing;
a radial compression mechanism communicatively coupled and moveable in relation to the housing, wherein the radial compression member has a cylindrical disc configuration with a variable diameter center aperture adapted for receiving the article to be engaged; a plurality of segments, each segment having a distal end area and a proximal end area, the segment distal end areas defining the center aperture, the distal end areas of each segment being movably coupled to the housing and the proximal end areas of each segment are movably coupled to the rotatable member, the distal end areas of each segment also being movably coupled to the housing by pins disposed through the distal end area of the segment and coupled to at least one point on the housing and wherein the proximal end areas of each segment are movably coupled to the rotatable member by pins disposed through the proximal end area of the segment and coupled to at least one point on the rotatable member, and each segment having a centerline between the proximal and distal ends, each segment having a proximal point and a distal point, the distal point being disposed on the centerline and the proximal point being disposed off the centerline, the proximal point being pivotally coupled to the housing and the distal point being pivotally coupled to the rotatable member; and a hand operable actuator communicatively coupled to the housing and the rotatable member.

2. The apparatus of claim 1, wherein the housing has a body with at least one central aperture adapted to receive the article to be engaged.

3. The apparatus of claim 2, wherein the housing body is cylindrical and the central aperture is axially disposed therein.

4. The apparatus of claim 1, wherein the radial compression mechanism and the rotatable member are at least partially enclosed in the housing.

5. The apparatus of claim 1, wherein the rotatable member has a ring configuration.

6. The apparatus of claim 5, wherein the rotatable member at least partially surrounds the radial compression mechanism.

7. The apparatus of claim 5, wherein the rotatable member is at least partially enclosed in the housing and has a circumference which is slightly less than an interior diameter of the housing.

8. The apparatus of claim 5, wherein the rotatable member has an arm member which is communicatively coupled to the actuator.

9. The apparatus of claim 1, wherein the segments are arranged so that the segment distal ends are disposed adjacent to and a predetermined distance away from a central point, and that the segment centerlines extending therefrom toward the segment distal ends are oriented away from the central point; and the segment distal ends moving closer to the central point upon rotation of the rotatable member in a predetermined direction.

10. The apparatus of claim 1, wherein the actuator is coupled to the rotatable member by a cam linkage connected to at least one arm and to the rotatable member.

11. The apparatus of claim 10, wherein the actuator further comprises a first arm connected cam linkage, and a second arm connected to the cam linkage and movable in relation to the first arm member.

12. A hand actuatable apparatus for radially engaging and compressing an article, comprising:

(a) a housing including a cylindrical body with at least one axially disposed central aperture adapted to receive the article to be engaged;

(b) at least one rotatable member communicatively coupled and moveable in relation to the housing, the rotatable member having a ring configuration which at least partially surrounds a radial compression member, the rotatable member further having an arm member;

(c) the radial compression mechanism communicatively coupled and moveable in relation to the housing, the radial compression member comprising a plurality of segments, each having a predetermined shape with a proximal end and a distal end, each segment having a centerline between the proximal and distal ends, each segment having a proximal point and a distal point, one said point being disposed on the centerline and one said point being disposed off the centerline, and one said point being pivotally coupled to the housing and one said point being pivotally coupled to the rotatable member, the segments being arranged so that the segment distal ends are disposed adjacent to and a predetermined distance away from a central point, and that the segment centerlines extending therefrom toward the segment distal ends are oriented away from the central point, and the segment distal ends moving closer to the central point upon rotation of the rotatable member in a predetermined direction; and (d) a hand operable actuator communicatively coupled to the housing and the rotatable member, the actuator comprising a cam linkage connected to the arm member of the rotatable member, a first arm connected to the cam linkage, and a second arm connected to the cam linkage and movable in relation to the first arm member.

13. An apparatus for engaging an article, comprising:

a housing;

at least one rotatable member communicatively coupled and moveable in relation to the housing;

a radial compression mechanism communicatively coupled and moveable in relation to the housing, wherein the radial compression member has a cylindrical disc configuration with a variable diameter center aperture adapted for receiving the article to be engaged; a plurality of segments, each segment having a distal end area and a proximal end area, the segment distal end areas defining the center aperture, the distal end areas of each segment being movably coupled to the housing and the proximal end areas of each segment are movably coupled to the rotatable member, the distal end areas of each segment also being movably coupled to the housing by pins disposed through the distal end area of the segment and coupled to at least one point on the housing and wherein the proximal end areas of each segment are movably coupled to the rotatable member by pins disposed through the proximal end area of the segment and coupled to at least one point on the rotatable member, each segment having a centerline between the proximal and distal ends, each segment having a proximal point and a distal point, the proximal point being disposed on the centerline and the distal point being disposed off the centerline, the proximal point being pivotally coupled to the housing and the distal point being pivotally coupled to the rotatable member; and a hand operable actuator communicatively coupled to the housing and the rotatable member.

14. The apparatus of claim 13, wherein the segments are arranged so that the segment distal ends are disposed adjacent to and a predetermined distance away from a central point, and that the segment centerlines extending therefrom toward the segment distal ends are oriented away from the central point; and the segment distal ends moving closer to the central point upon rotation of the rotatable member in a predetermined direction.

15. An apparatus for engaging an article, comprising:

a housing;

at least one rotatable member communicatively coupled and moveable in relation to the housing;

a radial compression mechanism communicatively coupled and moveable in relation to the housing, wherein the radial compression mechanism comprises:

a plurality of segments, each having a predetermined shape with a proximal end and a distal end, each segment having a centerline between the proximal and distal ends, each segment having a proximal point and a distal point, one said point being disposed on the centerline and one said point being disposed off the centerline, and one said point being pivotally coupled to the stationary member and one said point being pivotally coupled to the rotatable member;

the segments being arranged so that the segment distal ends are disposed adjacent to and a predetermined distance away from a central point, and that the segment centerlines extending therefrom toward the segment distal ends are oriented away from the central point; and the segment distal ends moving closer to the central point upon rotation of the rotatable member in a predetermined direction; and a hand operable actuator communicatively coupled to the housing and the rotatable member.

* * * * *